(12) United States Patent  
Jenkins et al.

(10) Patent No.: US 10,569,060 B2  
(45) Date of Patent: Feb. 25, 2020

(54) GUIDE CATHETERS WITH GUIDEWIRE DEFLECTION FEATURES

(71) Applicant: Acclarent, Inc., Menlo Park, CA (US)

(72) Inventors: Thomas R. Jenkins, Alameda, CA (US); Randy J. Kesten, Mountain View, CA (US); Jessica M. Liberatore, San Mateo, CA (US); Mina W. Chow, Campbell, CA (US)

(73) Assignee: Acclarent, Inc., Irvine, CA (US)

( * ) Notice: Subject to any disclaimer, the term of this patent is extended or adjusted under 35 U.S.C. 154(b) by 1135 days.

(21) Appl. No.: 14/792,939

(22) Filed: Jul. 7, 2015

(65) Prior Publication Data

US 2016/0015944 A1     Jan. 21, 2016

Related U.S. Application Data

(60) Provisional application No. 62/051,460, filed on Sep. 17, 2014, provisional application No. 62/022,445, filed on Jul. 9, 2014.

(51) Int. Cl.
     *A61M 25/09*      (2006.01)
     *A61M 29/02*      (2006.01)

(52) U.S. Cl.
     CPC ...... *A61M 25/09041* (2013.01); *A61M 29/02* (2013.01); *A61M 2025/09175* (2013.01); *A61M 2210/0675* (2013.01); *A61M 2210/0681* (2013.01)

(58) Field of Classification Search
     CPC .......... A61M 25/0108; A61M 25/0068; A61M 25/0662; A61M 25/09041; A61M 25/0169; A61M 25/06; A61M 25/065; A61M 25/0172; A61M 25/09175; A61M 2025/0183; A61M 25/0062; A61M 2210/0681; A61M 29/02; A61B 1/00183; A61B 17/24

See application file for complete search history.

(56) References Cited

U.S. PATENT DOCUMENTS 5,730,742 A * 3/1998 Wojciechowicz ..... A61B 18/14
                                                              604/35
2006/0063973 A1 * 3/2006 Makower ........... A61B 1/00135
                                                              600/114

(Continued)

FOREIGN PATENT DOCUMENTS

WO     WO 2014/072977 A1     5/2014

OTHER PUBLICATIONS

International Search Report and Written Opinion dated Oct. 28, 2015 for International Application No. PCT/US2015/039508, 19 pages.

(Continued)

*Primary Examiner* — Imani N Hayman
*Assistant Examiner* — Tiffany Legette
(74) *Attorney, Agent, or Firm* — Frost Brown Todd LLC

(57) ABSTRACT

A guide catheter system for use in treating the sinus cavity or Eustachian tube is described. The system includes a guide catheter that has a proximal end and a distal end and an elongate shaft between the proximal end and the distal end and a guidewire. The guide catheter includes a deflection feature on a distal tip of the distal end for deflecting the guidewire at a predetermined angle.

30 Claims, 10 Drawing Sheets

(56) References Cited

U.S. PATENT DOCUMENTS

| | | |
|---|---|---|
| 2007/0167682 A1* | 7/2007 | Goldfarb .............. A61B 1/0014 |
| | | 600/114 |
| 2007/0293726 A1 | 12/2007 | Goldfarb et al. |
| 2010/0030031 A1 | 2/2010 | Goldfarb et al. |
| 2010/0152706 A1* | 6/2010 | Morris .................. A61M 1/008 |
| | | 604/523 |
| 2010/0241155 A1* | 9/2010 | Chang .................... A61B 17/24 |
| | | 606/196 |
| 2011/0004057 A1 | 1/2011 | Goldfarb et al. |
| 2012/0071856 A1 | 3/2012 | Goldfarb et al. |
| 2012/0071857 A1* | 3/2012 | Goldfarb ................ A61B 17/24 |
| | | 604/514 |
| 2012/0078118 A1 | 3/2012 | Jenkins et al. |

OTHER PUBLICATIONS

International Preliminary Report on Patentability dated Jan. 10, 2017 for International Application No. PCT/US2015/039508, 11 pages.

U.S. Appl. No. 61/725,523 entitled, "Inflator for Dilation of Anatomical Passageway," filed Nov. 13, 2012.

\* cited by examiner

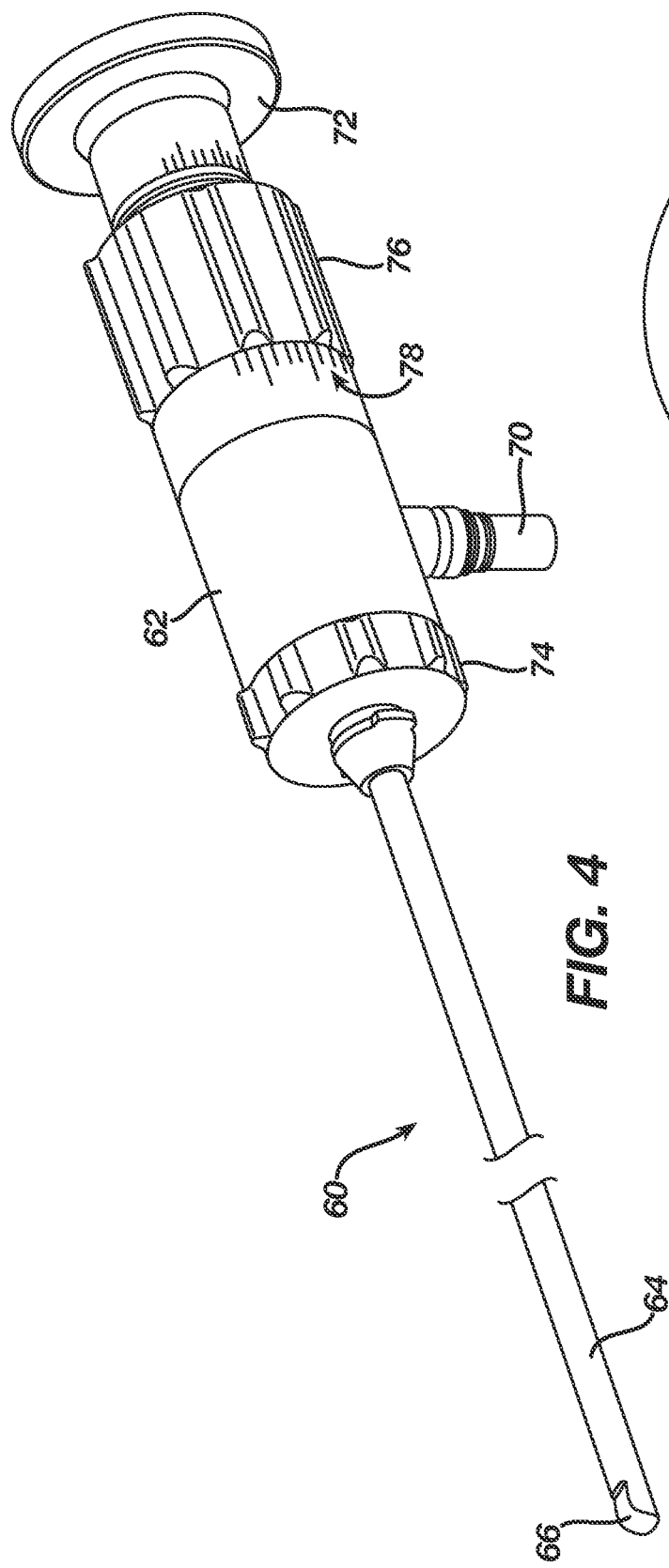
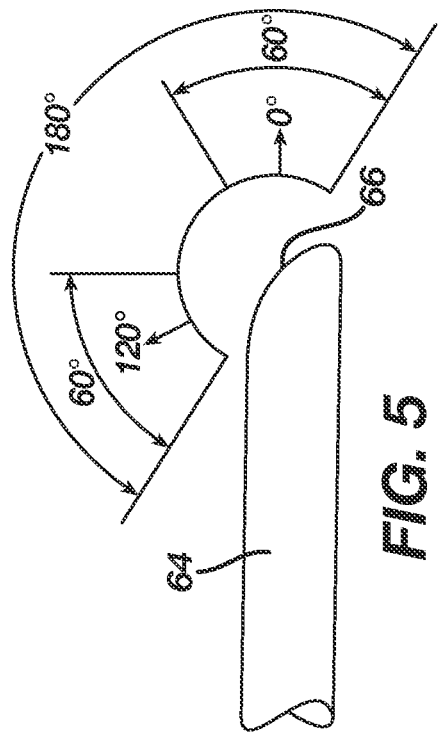
FIG. 4
FIG. 5

FIG. 11B  FIG. 11C

GUIDE CATHETERS WITH GUIDEWIRE DEFLECTION FEATURES

FIELD OF THE INVENTION

The present invention is generally related to medical devices and apparatus and in particular, for devices for dilating an anatomical passageway in the ear, nose or throat.

BACKGROUND OF THE INVENTION

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

SUMMARY OF THE INVENTION

In one embodiment, the invention is directed to a guide catheter system for use in treating a sinus cavity or a Eustachian tube. The system includes a guide catheter that has a proximal end and a distal end and an elongate shaft between the proximal end and the distal end and a guidewire. The guide catheter includes a deflection feature on a distal tip of the distal end for deflecting the guidewire at a predetermined angle.

In one aspect, the deflection feature may be a groove, a wedge, a hood or a probe. In another aspect, the guide catheter distal end has an oval-shaped opening. The oval-shaped opening may have a width of between 2 mm and 3 mm and a length of between 3 mm and 6 mm or a width of between 2 mm and 3 mm and a length of between 5 mm and 9 mm. In another aspect, the deflection feature retains the guidewire in the center of the oval-shaped opening.

In another aspect, the sinus cavity is the maxillary sinus cavity and the deflection feature is a groove for deflecting the guidewire at an angle of between 105° and 130°.

In a further aspect, the sinus cavity is the frontal sinus cavity and the deflection feature is a groove for deflecting the guidewire at an angle of between 60° and 85°.

In yet another aspect, the sinus cavity is the sphenoid sinus cavity and the deflection feature is a wedge for deflecting the guidewire at an angle of between 5° and 25°.

In another aspect, the deflection feature comprises a hood and may optionally comprise a support member.

In a further aspect, the deflection feature comprises a probe for identifying an ostia of the sinus cavity and for deflecting the guidewire toward the ostia.

In another embodiment, the invention is directed to a method for deflecting a guidewire to a predetermined angle. The method includes providing a guide system the guide system having a guide catheter and a guidewire. The guide catheter has a deflection feature for deflecting the guidewire to a predetermined angle. The guide system is inserted into a patient's nasal cavity and the guidewire is advanced such that it is deflected at a predetermined angle toward a desired sinus cavity.

In a further embodiment, the invention is directed to a guide catheter system for use in treating a sinus cavity or a Eustachian tube. The system includes a guide catheter having a proximal end and a distal end and an elongate shaft between the proximal end and the distal end, and a guidewire having a proximal end and a distal end and a bent distal portion near the distal end that is bent at an angle of β from the remaining portion of the guidewire. The guidewire further includes a marker on the bent distal portion of the guidewire to allow visualization of the direction of the bent distal portion in relation to the remaining portion of the guidewire. In another aspect, the guide catheter comprises a distal end profile and a proximal end profile, the distal end profile being smaller than the proximal end profile.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4 depicts a perspective view of an exemplary endoscope suitable for use with the dilation catheter system of FIG. 1;

FIG. 5 depicts a side elevational view of the distal end of the endoscope of FIG. 4, showing an exemplary range of viewing angles;

FIG. 11B depicts a view of the proximal opening of the guide catheter system of FIG. 11A;

FIG. 11C depicts a view of the distal opening of the guide catheter system of FIG. 11A;

Figure 1:
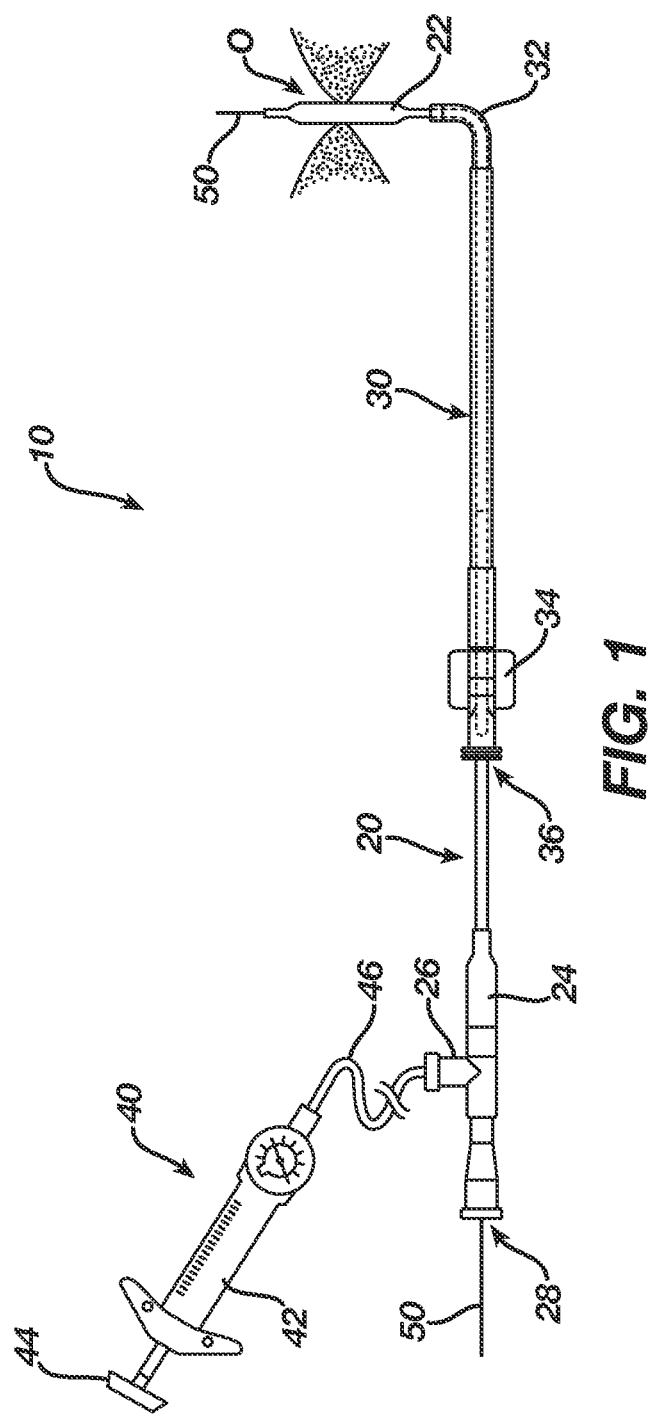
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilation catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

Figure 2:
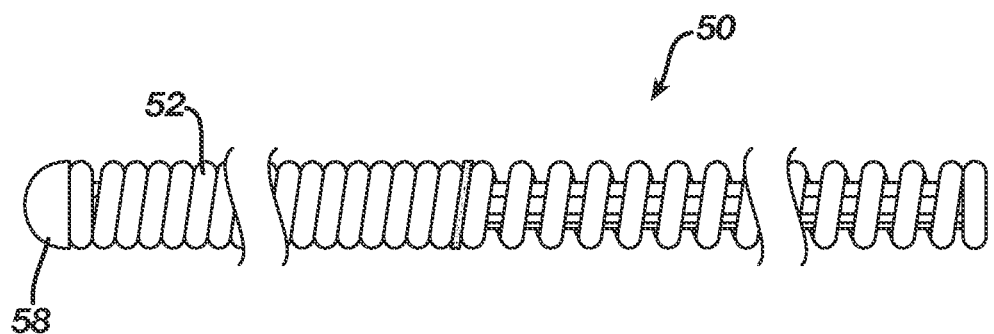
FIG. 2 depicts a side elevational view of an exemplary illuminating guidewire suitable for use with the dilation catheter system of FIG. 1.
Figure 3:
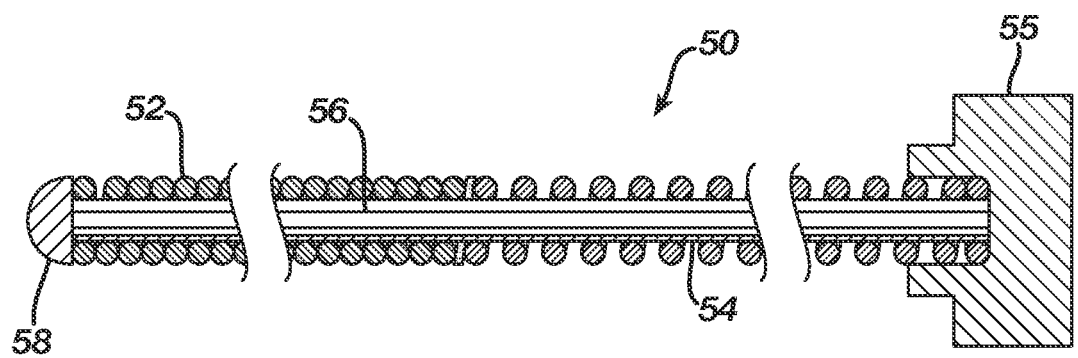
FIG. 3 depicts a side cross-sectional view of the illuminating guidewire of FIG. 2.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (0). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (0) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (0) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (0) (or some other targeted anatomical passageway). After dilator (22) has been positioned within the ostium (0), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (0), such as by remodeling the bone, etc., forming ostium (0). By way of example only, dilator (22) may be inflated to a volume sized to achieve about 10 to about 12 atmospheres. Dilator (22) may be held at this volume for a few seconds to sufficiently open the ostium (0) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

Although described with regard to the sinus opening, the inventions described herein may also be useful for the dilation of the Eustachian tube, repair of endo-cranial fractures, airway procedures such as subglottic stenosis dilation and other procedures of the ear, nose and throat.

III. Exemplary Guide Catheter Systems

A. Exemplary Maxillary Guide Catheter Systems

FIGS. 6A-6E show one merely illustrative example of an exemplary maxillary guide catheter system (100) according to the invention. This guide catheter system (100) provides for optimal guidewire deflection for positioning of the guidewire toward the maxillary sinus in an atraumatic fashion, that is, without damaging the tissue of the maxillary sinus and maxillary sinus passageway.

Figure 6A:
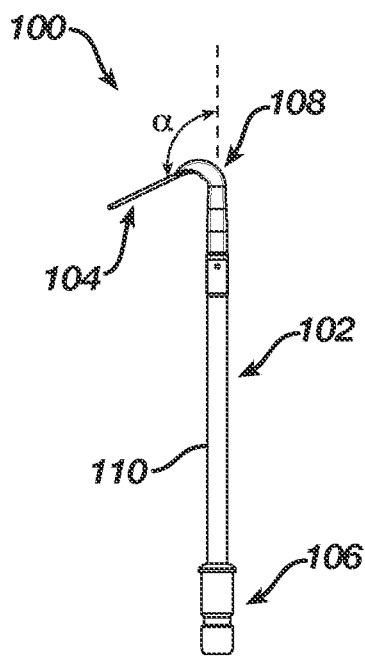
FIG. 6A depicts a side view of an exemplary maxillary guide catheter system according to the invention.
Figure 6B:
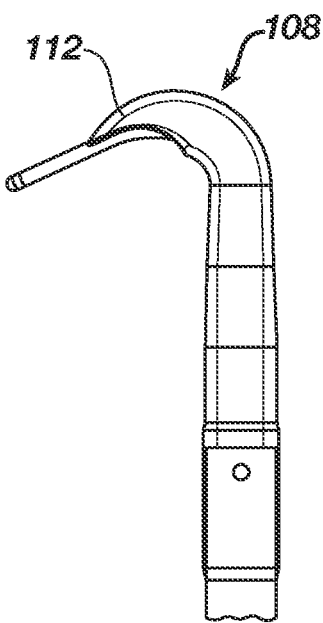
FIG. 6B depicts an enlarged side view of the distal end of the exemplary guide catheter system of FIG. 6A.

As shown in FIGS. 6A and 6B, the guide catheter system (100) includes a maxillary guide catheter (102) and a guidewire (104). The guide catheter (102) has a proximal end (106), a distal end (108) and an elongate shaft (110) between the proximal end (106) and the distal end (108). The distal end (108) is particularly designed for the maxillary sinus with a hooked shape distal tip (112) to slide around the uncinate process and to direct the guidewire at a predetermined angle α, in this case between about 105° and 130°, or between 110° and 115° or approximately 115° (115° plus or minus 5°) from the elongate shaft.

Figure 6C:
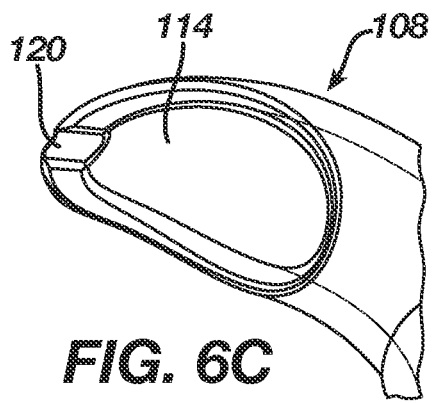
FIG. 6C depicts a further enlarged view of the distal opening of the maxillary guide catheter of the guide catheter system of FIG. 6A.
Figure 9:
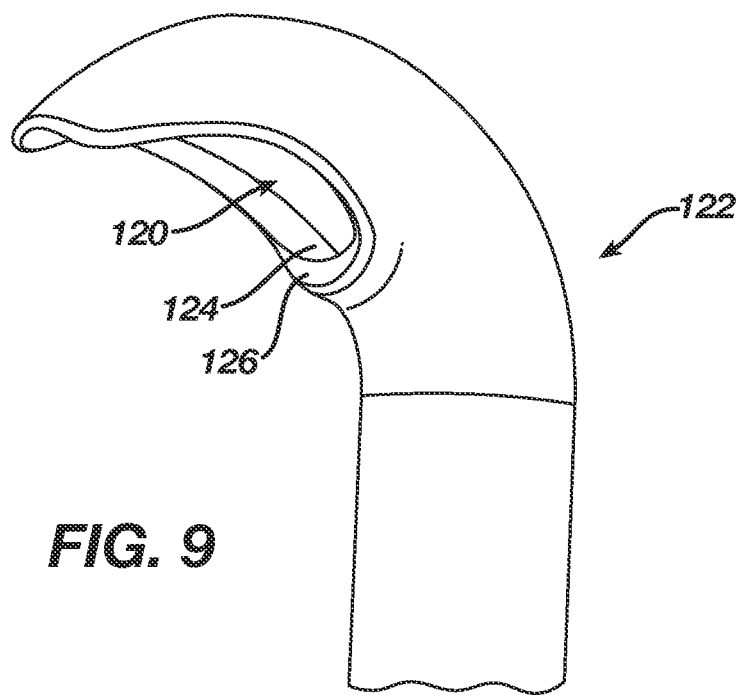
FIG. 9 depicts an enlarged view of the distal opening of a further exemplary maxillary guide catheter according to the invention.

The distal end (108) of the guide catheter (102) is shown in an enlarged view in FIG. 6C. The guide catheter distal end (108) contains an oval shaped opening (114). This large-mouthed opening (114) allows for better visualization of the target anatomy and easy balloon catheter advancement and retraction. The size and shape of the opening (114) assists in proper folding of the balloon of the balloon catheter during the initial retraction and thereafter. The oval-shaped opening (114) may further include trumpet-shaped edges to avoid damage to the balloon and further assist in proper folding of the balloon during retraction into the lumen of the guide catheter (102). As further shown in FIG. 9, a trumpet-shaped edge is used herein to reference a flared distal end of the oval-shaped opening (114). It is intended that the conical distal large mouthed opening (120) of the guide catheter (122) flares out as it progresses distally such that the inside surface of the guide-catheter (124) becomes the outside surface (126) of the guide catheter system, where the surface is smooth and without sharp edges for ease in balloon insertion and retraction.

Exemplary balloon sizes for the balloon catheters useful in the guide catheter system of the invention include those that are be 5 mm×16 mm, 6 mm×16 mm and 7 mm×16 mm, or they may be 3.5 mm×12 mm, 5 mm×24 mm, 6 mm×24 mm, or 7 mm×24 mm, although others are within the scope of the invention, including, but not limited to 5 mm×16 mm, 5 mm×24 mm or 7 mm×16 mm. The balloon inflated diameters for the medical devices are as follows: 3.5 mm for the 3.5 mm×12 mm, 5 mm for the 5 mm×16 mm and the 5 mm×24 mm, 6 mm for the 6 mm×16 mm and 6 mm×24 mm, and 7 mm for the 7 mm×24 mm. The balloon inflated working lengths for the medical devices are as follows: 12 mm for the 3.5 mm×12 mm, 16 mm for the 5 mm×16 mm, 6 mm×16 mm and 7 mm×16 mm and 24 mm for the 5 mm×24 mm, 6 mm×24 mm and 7 mm×24 mm. The deflation time of the balloon catheter is less than about 30 seconds and often 5 seconds or less.

The balloon is made of any suitable material known in the art for inflation balloons and may be constructed or semi-compliant or non-compliant materials such as nylon (semi-compliant) and polyethylene terephthalate (PET) (non-compliant). In a particular embodiment, the balloon is constructed of nylon.

Figure 6D:
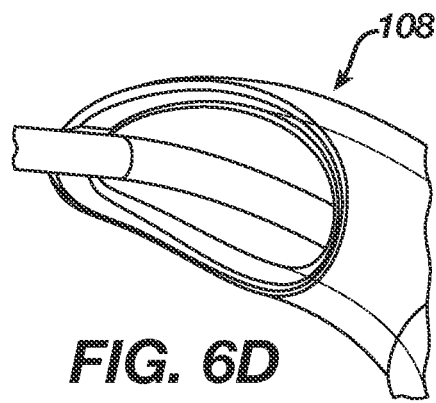
FIG. 6D depicts the enlarged view of the distal opening of the maxillary guide catheter of FIG. 6C and further incorporation the guidewire of the system of FIG. 6A.

Referring again to FIG. 6C, the distal tip (112) of the guide catheter (102) further includes a guidewire deflection feature (120). In this case, the guidewire deflection feature (120) is a groove in the distal tip (112) which also serves as a retention feature. During initial insertion of the guide catheter (102) into the sinus anatomy, the guidewire is retracted within the guide catheter. As shown in FIG. 6D, once the guide catheter is properly in positioned within the sinus anatomy, the guidewire is extended and positioned within the guidewire deflection feature (120). The guidewire (104) is retained in the guidewire deflection feature (120) and is prevented from lateral movement as it slides in the guidewire deflection feature (120) when advanced distally or retracted proximally through the guide catheter (102) thereby facilitating the centering of the guidewire (104) within the opening (114) of the guide catheter (102).

Figure 6E:
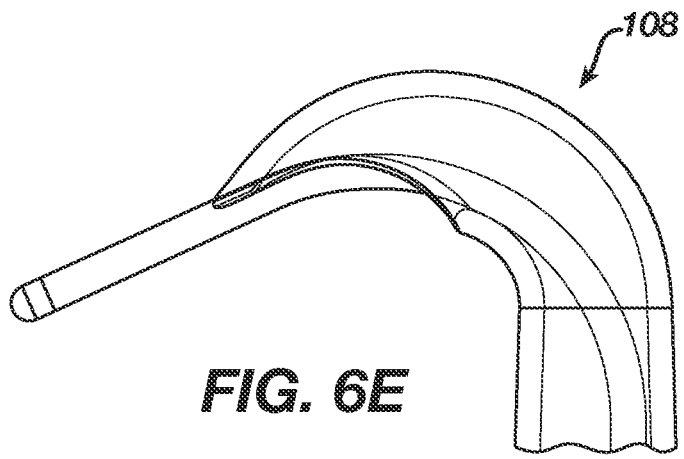
FIG. 6E depicts a further enlarged side view of the distal of the maxillary guide catheter system shown in FIG. 6A.

As shown in FIG. 6E, the catheter system of FIG. 6A is included with a translucent image of the guide catheter (102) to better see the trajectory of the guidewire (104). The distal tip (112) of the guide catheter (102) is further dimensioned to optimize positioning of the guidewire toward the maxillary sinus and deflection of the guidewire (104) as it exits from the distal end (108) of the guide catheter (102). The positioning of the guidewire (104) in the deflection feature (120) and the geometry of the oval opening (114) provide for the 115° trajectory noted above. The oval-shaped opening may have a width of between 2 mm and 3 mm and a length of between 3 mm and 6 mm. In a particular embodiment of the invention the oval-shaped opening is 2.7 mm in width and 5 mm in length.

B. Exemplary Frontal Guide Catheter Systems

FIGS. 7A-7D show an illustrative example of a frontal guide catheter system (200) according to the invention. This guide catheter system (200) provides for optimal guidewire deflection for positioning of the guidewire toward the frontal sinus in an atraumatic fashion, that is, without damaging tissue of the frontal sinus or frontal sinus passageway.

Figure 7A:
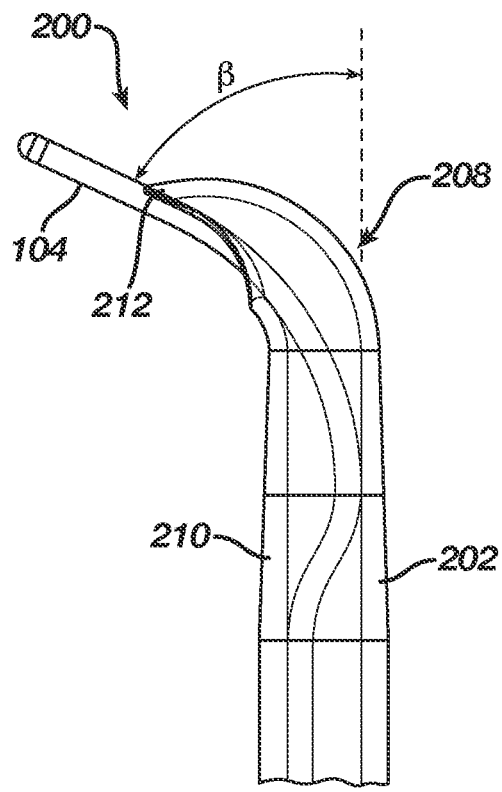
FIG. 7A depicts a side view of an exemplary frontal guide catheter system according to the invention.

As shown in a translucent manner in FIG. 7A, the guide catheter system (200) includes a frontal guide catheter (202) and a guidewire (104). The guide catheter (202) has a proximal end (not shown, but identical to the proximal end (106) of the maxillary guide catheter (102)), a distal end (208) and an elongate shaft (210) between the proximal end (not shown) and the distal end (208). The distal end (208) is particularly designed for the frontal sinus to direct the guidewire at a predetermined angle β, in this case between about 60° and 85°, or between 65° and 75° or approximately 70° (70° plus or minus 5°) from the elongate shaft (210).

Figure 7B:
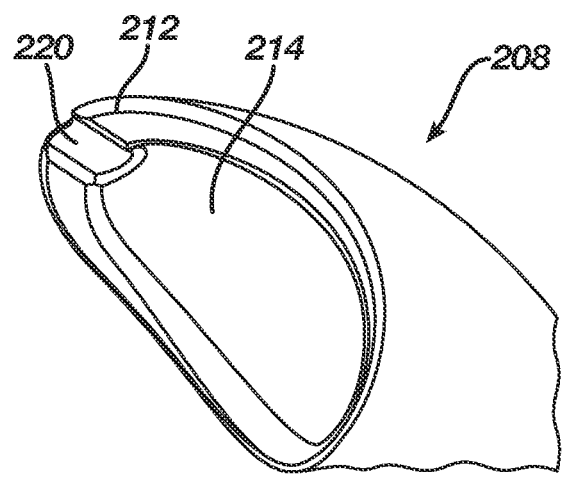
FIG. 7B depicts a further enlarged view of the distal opening of the frontal guide catheter of the guide catheter system of FIG. 7A.

The distal end (208) of the guide catheter (202) is shown in an enlarged view in FIG. 7B.

The guide catheter distal end (208) contains an oval shaped opening (214). This large-mouthed opening (214) allows for better visualization of the target anatomy and for easy balloon catheter advancement and retraction and ensures proper folding of the balloon of the balloon catheter during the initial retraction. The oval-shaped opening (214) may further include trumpet-shaped edges to avoid damage to the balloon and further assist in proper folding of the balloon during retraction into the lumen of the guide catheter (202).

Referring again to FIG. 7B, the distal tip (212) of the guide catheter (102) further includes a guidewire deflection feature (220). In this case, the guidewire deflection feature (220) is a groove in the distal tip (212) which also serves as a retention feature. During initial insertion of the guide catheter (202) into the sinus anatomy, the guidewire is retracted within the guide catheter. As shown in FIG. 7D once the guide catheter is properly in positioned within the sinus anatomy, the guidewire is extended and positioned within the guidewire deflection feature (220). The internal spring structure of the guidewire (204) forces the guidewire to be retained in the guidewire deflection feature (220) and is prevented from lateral movement as it slides in the guidewire deflection feature (220) when advanced distally or retracted proximally through the guide catheter (202) thereby facilitating the centering of the guidewire (104) within the opening (214) of the guide catheter (202).

Figure 7C:
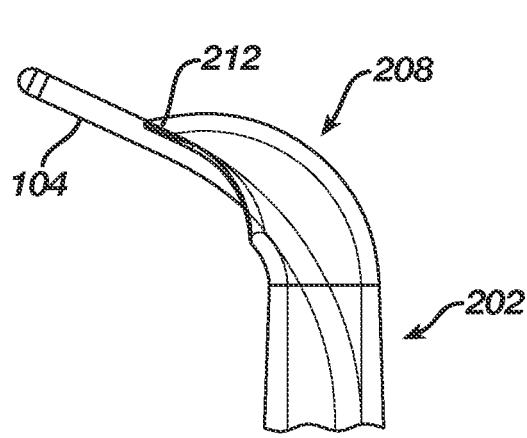
FIG. 7C depicts an enlarged side view of the distal end of the exemplary guide catheter system of FIG. 7A.
Figure 7D:
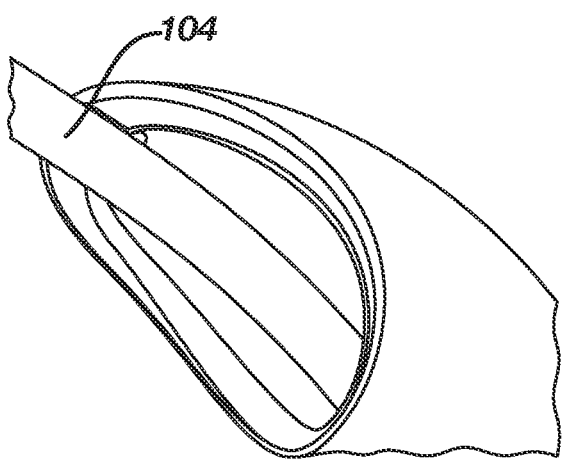
FIG. 7D depicts an enlarged view of the distal opening of the frontal guide catheter of FIG. 7C and further incorporating the guidewire of the system of FIG. 7A.

As shown in FIG. 7C, the distal tip (212) of the guide catheter (202) is further dimensioned to optimize positioning of the guidewire toward the frontal sinus and deflection of the guidewire (104) as it exits from the distal end (208) of the guide catheter (202). The positioning of the guidewire (104) in the deflection feature (220) and the geometry of the oval opening (214) provide for the 70° trajectory noted above. The oval-shaped opening may have a width of between 2 mm and 3 mm and a length of between 3 mm and 6 mm. In a particular embodiment of the invention the oval-shaped opening is 2.7 mm in width and 4.5 mm in length.

C. Exemplary Sphenoid Guide Catheter Systems

Figure 8A:
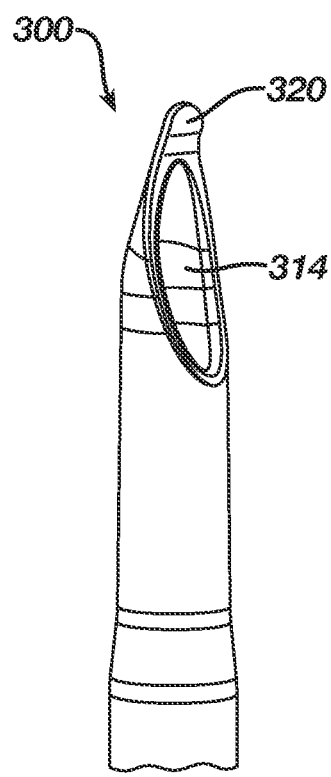
FIG. 8A depicts an enlarged view of the distal opening of a sphenoid guide catheter according to the invention.
Figure 8B:
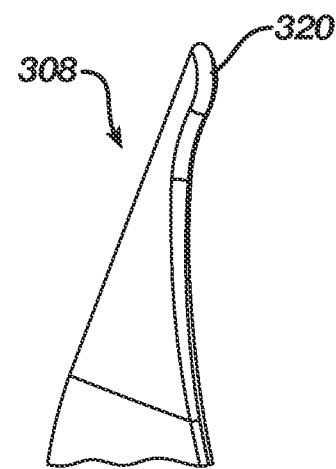
FIG. 8B depicts a side view of the distal end of the sphenoid guide catheter shown in FIG. 8A.
Figure 8C:
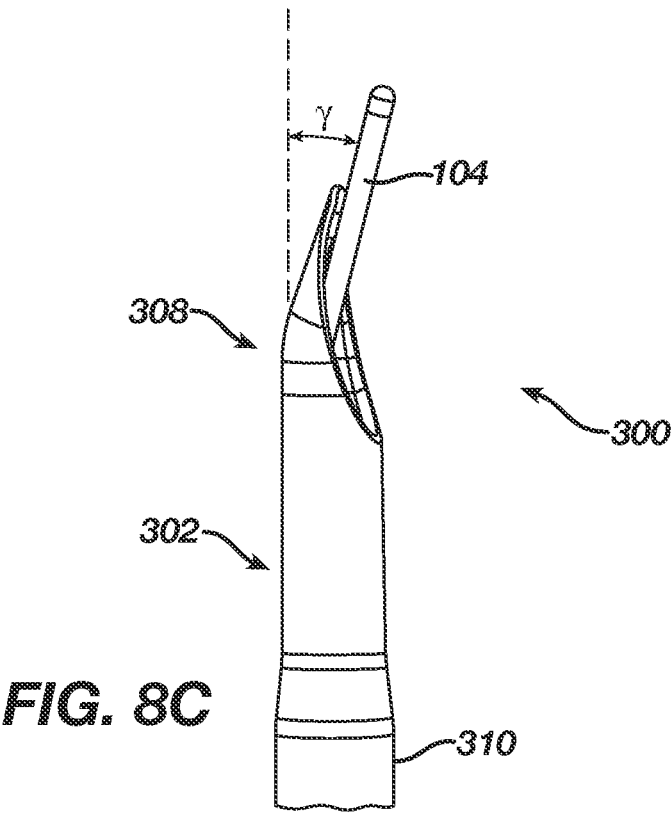
FIG. 8C depicts a side view of the sphenoid guide catheter shown in FIG. 8A and a guidewire in a guide catheter system according to the invention.

FIGS. 8A-8C show one merely illustrative example of an exemplary sphenoid guide catheter system (300) according to the invention. This guide catheter system (300) provides for optimal guidewire deflection for positioning of the guidewire toward the sphenoid sinus in an atraumatic fashion, that is, without damaging tissue of the sphenoid sinus or sphenoid sinus passageway.

As shown in FIG. 8C, the guide catheter system (300) includes a sphenoid guide catheter (302) and a guidewire (104). The guide catheter (302) has a proximal end (not shown, but identical to the proximal end (106) of the maxillary guide catheter (102)), a distal end (308) and an elongate shaft (310) between the proximal end (not shown) and the distal end (308). The distal end (308) is particularly designed for the sphenoid sinus to be in a wedge shape, to direct the guidewire to the side wall of the sphenoid sinus at a predetermined angle γ, in this case between about 5° and 25°, or between 10° and 20° or approximately 15° (15° plus or minus 5°) from the elongate shaft and to better visualize the movement and placement of the guidewire (104) toward the sinus cavity. The wedge shape further enables movement and placement of the guide catheter (302) toward the sphenoid sinus cavity without damaging tissue in the passageway.

The distal end (308) of the guide catheter (302) is shown in an enlarged view in FIG. 8B. As shown in FIG. 8C, the guide catheter distal end (308) contains an oval shaped opening (314). This large-mouthed opening (314) allows for better visualization of the target anatomy and for easy balloon catheter advancement and retraction and ensures proper folding of the balloon of the balloon catheter during the initial retraction. The oval-shaped opening (314) may further include trumpet-shaped edges to avoid damage to the balloon and further assist in proper folding of the balloon during retraction into the lumen of the guide catheter (302) thereby facilitating the centering of the guidwire (104) within the opening (314) of the guide catheter (302).

Referring again to FIG. 8A, the distal tip (312) of the guide catheter (302) further includes a guidewire deflection feature (320). In this case, the guidewire deflection feature (320) is a wedge in the distal tip (312). During initial insertion of the guide catheter (302) into the sinus anatomy, the guidewire is refracted within the guide catheter. As shown in FIG. 8C once the guide catheter is properly in positioned within the sphenoid sinus anatomy, the guidewire is extended. As shown in FIG. 8C, the guidewire (104) is deflected by the guidewire deflection feature (320) toward the sphenoid sinus cavity during distal advancement of the guidewire.

As shown in FIG. 8C, the distal tip (312) of the guide catheter (302) is further dimensioned to optimize positioning of the guidewire toward the sphenoid sinus and deflection of the guidewire (104) as it exits from the distal end (308) of the guide catheter (302). The positioning of the guidewire (104) on the deflection feature (320) and the geometry of the oval opening (314) provide for the 15° trajectory noted above. The oval-shaped opening may have a width of between 2 mm and 3 mm and a length of between 5 mm and 9 mm. In a particular embodiment of the invention the oval-shaped opening is 2.7 mm in width and 7.0 mm in length.

D. Alternative Exemplary Maxillary Guide Catheter Systems

Figure 10:
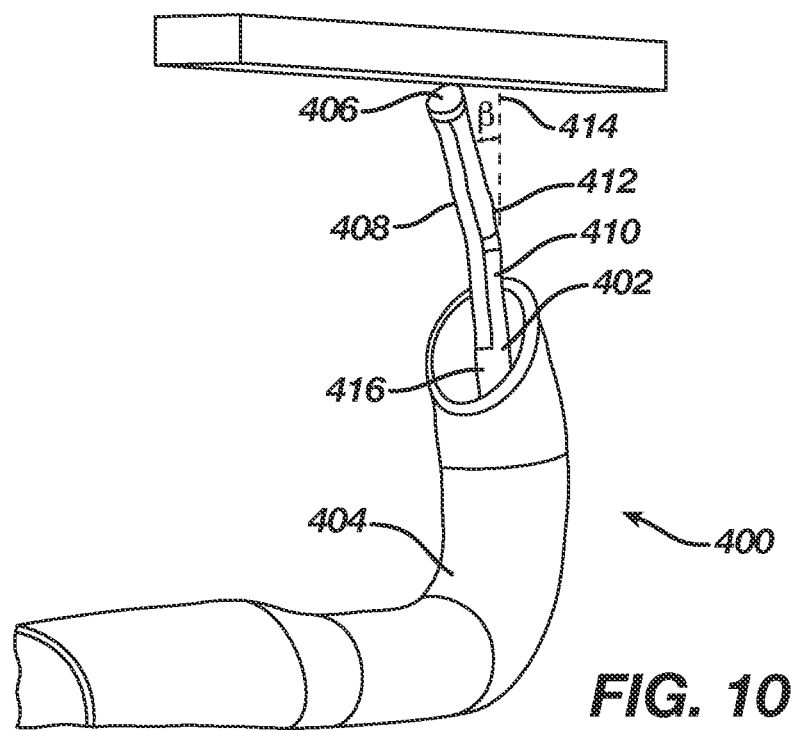
FIG. 10 depicts a side view of an exemplary maxillary guide catheter system according to a further embodiment of the invention.

An alternative method of providing for appropriate guidewire deflection is shown, for example, in FIG. 10. A guide catheter assembly (400) includes a guidewire (402) and a guide catheter (404). The guidewire (402) may be a Relieva Luma Sentry guidewire (Acclarent, Inc, Menlo Park, Calif.) with a of predetermined bend angle β measured from the outside face (412) of the bend angle β of the guidewire (402) to a line (416) the defines the straight portion of the guidewire (402), in the case of Luma Sentry, an angle of 20 degrees or between 10 and 30 degrees near its distal tip (406), or other similar guidewire that is an illuminating or non-illuminating guidewire known to those of skill in the art. The 20 degree bend allows the user to steer the wire in different directions by rotating and advancing the guidewire (402). However, when advancing the guidewire (402) around the uncinate and into the maxillary sinus, it is difficult to see the direction of the bent distal end (410) as it is advanced out of the guide catheter (404). By the time enough of the guidewire (402) has protruded from the guide catheter (404) such that the entire bent distal portion (410) is visible, the distal tip (406) of the wire is around the uncinate and out of sight. A bent distal portion (410) that is pointed anteriorly (toward the ostium of the maxillary sinus), will allow the guidewire (402) to more reliably enter the infundibulum and enter the ostium. If the bent distal portion (410) is pointed posteriorly, the guidewire (402) may buckle and the bent distal portion (410) may be deflected away from the infundibulum and the ostium. The endoscopic marker (408) located on the inside face (416) of the angle β of the bent distal portion (410) of the guidewire (402) above and/or below the bend near the distal tip (406) of the guidewire (402) allows for endoscopic visualization of the direction of the bent portion (410) of guidewire (402). The endoscopic marker may be etched on the guidewire, for example by laser etching the coil or may be printed thereon and may have a length of from about 2 mm to about 20 mm, often about 5 mm. The maxillary guide catheter (404) deflects the guidewire (402) at an angle of 85 to 105 degrees, such that, including the 20 degree bend in the guidewire (402), the guidewire (402) is deflected between 105 and 125 degrees (rather than a deflection of 65 to 85 degrees if the bent distal portion (410) of the guidewire (402) is pointed in the opposite direction).

E. Guide Catheter Systems

The guide catheters described may be useful for dilation of the Eustachian Tube, repair of endo-cranial fractures, for airway procedures such as subglottic stenosis dilation and other procedures of the ear, nose and throat. For dilation of the Eustachian Tube, a 55 degree molded guide with an oval-shaped opening as described above may be useful to assist in balloon retraction and to facilitate visualization of the target area. The guide catheters may be made of a single piece of molded plastic (such as but not limited to nylon, polypropylene and polycarbonate) and would be intended for single use and easy disposability, or may be constructed primarily of stainless steel and be easily re-processable and reusable. The distal end of the guide catheter may include a colored plastic tip of lower durometer plastic (such as a blue Pebax (polyether block amide) tip), that is atraumatic to tissue and easily visible under endoscopic illumination. Alternatively, the guide catheter may include a stainless steel proximal portion and a plastic distal portion that is of lower durometer than the stainless steel portion, but is of higher durometer than the atraumatic distal tip.

The exemplary guide catheters may be used to replace the guide catheter provided with the Relieva® Spin Balloon Sinuplasty™ System by Acclarent, Inc. of Menlo Park, Calif. In that system, the guide catheter appropriate to treat the desired sinus cavity is attached to a handle such that a balloon catheter and illuminating guidewire are positioned within the guide catheter. The guide catheter is positioned within the nose and the guidewire is advanced to the appropriate position such that the balloon catheter can be advanced over the guidewire and the balloon of the balloon catheter positioned within the target anatomy, often the sinus ostium or the sinus passageway, and inflated to treat the target anatomy. The inflation procedure may be repeated. The balloon is then deflated and removed from the target anatomy. The procedure may be repeated or the balloon may be withdrawn into the guide catheter for removal from the target anatomy. The guidewire is also withdrawn and the guide catheter is removed from the nasal cavity.

Figure 16:
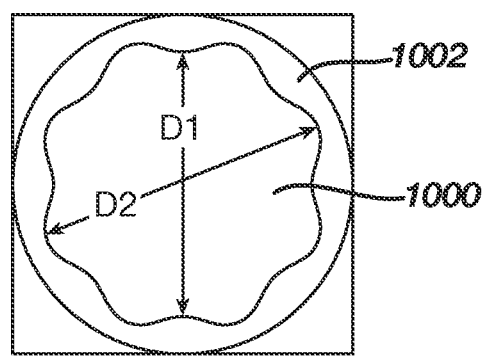
FIG. 16 depicts a cross-sectional view of an exemplary guide catheter according to the invention.

The exemplary guide catheter may further include a suction feature. The guide catheter provided with the Relieva® Spin Balloon Sinuplasty™ System contains a Polytetrafluoroethylene (PTFE) liner. The liner limits the clearance gap between the balloon catheter and the guide catheter lumen. In order to increase the clearance gap and improve the suction flow when the balloon catheter of the irrigation catheter is in place in the sinus cavity, the PTFE liner is removed and replaced with a guide lumen with a shape such as a petal shape, a hexagon, pentagon or other similar shape to provide clearance that is not blocked by the catheter shaft. The petal shape of the guide catheter lumen (1000) is as shown in FIG. 16. With this petal shape lumen design, the inner distance D1 can be the same as the inner diameter of the Relieva® Spin Balloon Sinuplasty™ System guide catheter (i.e. 0.093 inches). The outer distance D2 is larger than the inner diameter providing extra clearance for suction flow and less surface contact with the balloon catheter and/or irrigation catheter, thereby reducing catheter insertion and retraction friction. Although the wall thickness of the shaft (1002) is thinner in the D2 area, the guide shaft column strength is optimized to minimize the negative impact of varying the lumen (1002) shape design. The alternating small and large inner diameter design (D1 and D2) provides for reduced contact surface area between the balloon catheter and the guide catheter lumen. The thin wall zone associated with the large inner diameter D2 will allow for the flexing of that zone, thereby accommodating the fit of the balloon catheter as it passes through the bending curve of the guide catheter.

The exemplary guide catheter system may further include a detachable tip such that the same guide catheter can be used for multiple sinuses. In this embodiment, the edges of the distal end of the guide catheter and the proximal end of the detachable tip are crimped in order to allow the ends to overlap and to secure in place. Nylon inserts may be incorporated to improve the fit of the guide catheter and the detachable tip. Alternatively, a heat shrink material such as a polyether block amide polymer may be bonded to the distal end of the guide catheter and the proximal end of the detachable tip to provide for a stronger and more secure joint between the guide catheter and the detachable tip.

F. Alternative Exemplary Sphenoid Guide Catheter Systems

FIGS. 11A-11D show an illustrative example of an alternative exemplary sphenoid guide catheter (400) according to the invention. This guide catheter system (400) provides for guide catheter placement into tight anatomical regions and for removal and reinsertion of an endoscope in an atraumatic fashion, that is, without damaging tissue of the sphenoid sinus or sphenoid sinus passageway.

Figure 11A:
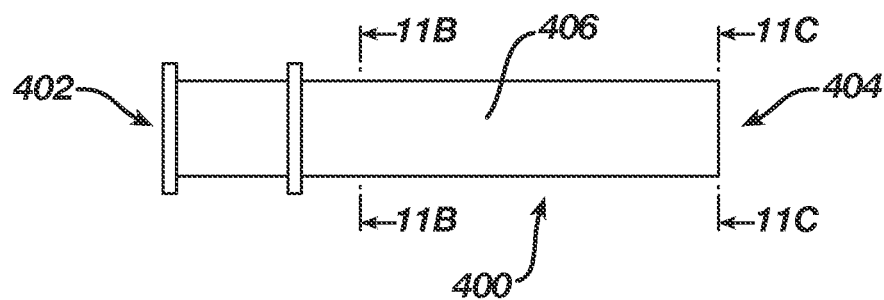
FIG. 11A depicts a top view of an exemplary guide catheter system according to the invention.
Figure 11D:
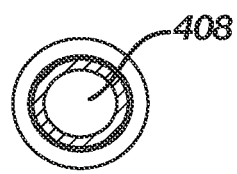
FIG. 11D depicts a side view of the exemplary guide catheter system of FIG. 11A.
Figure 11D:
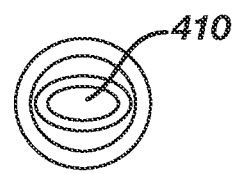
Figure 11D:
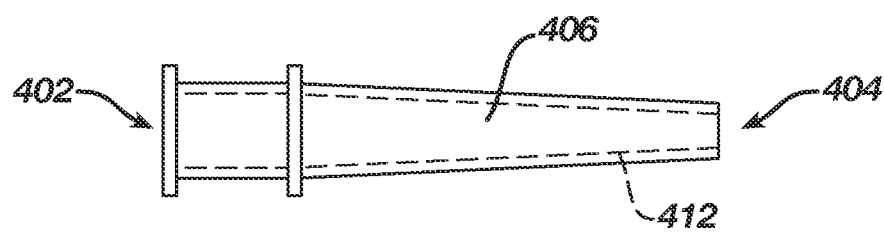

As shown in FIG. 11A, the guide catheter (400) has a proximal end (402) and distal end (404) and an elongate shaft (406) between the proximal end (402) and the distal end (404). The distal end (404) is particularly designed for the sphenoid sinus to have a smaller profile than that of the proximal end (406), the size of the openings are shown for comparison in FIG. 11 B, which shows the opening at the proximal end (408) and FIG. 11C which shows the opening at the distal end (410). The guide catheter (400) is constructed a soft polymeric material, i.e. from materials including but not limited to a polyether block amide polymer and nylon. A shape-memory material such as nitinol may be incorporated into the guide catheter (400) to permit shaping of the elongate shaft into the appropriate angle for the particular anatomy of the patient to be treated. FIG. 11D is a side view of the guide catheter (400) showing the tapering or the elongate shaft (406) when the guide catheter is in the closed position. Rigid spring members may be included on either side of the elongate shaft (406) to force the distal end (404) into the closed position shown most clearly in FIG. 11D. This closed position enables movement and placement of the guide catheter (400) toward the sphenoid sinus cavity without damaging tissue in the passageway. Following placement of the guide catheter (400) and endoscope, guidewire, and/or balloon catheter can be inserted into the proximal opening 408, opening up the lumen 412 of the elongate shaft 406 and applying pressure to the side wall of the mucosa without causing trauma.

Figure 12:
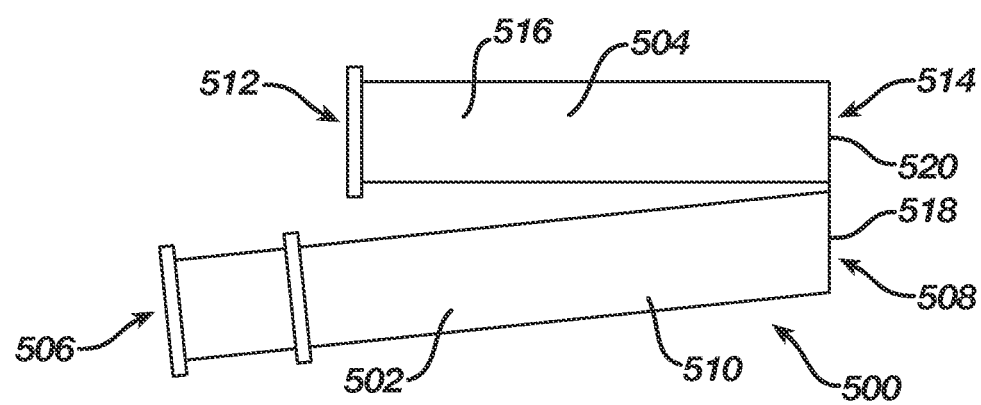
FIG. 12 depicts a top view of a further exemplary guide catheter system according to the invention.
Figure 13A:
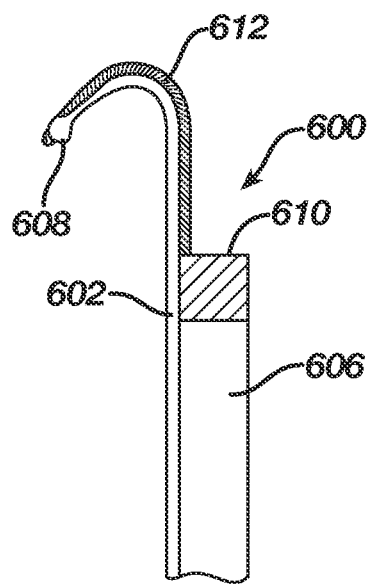
FIG. 13A depicts a side view of an exemplary guide catheter system according to the invention.
Figure 13B:
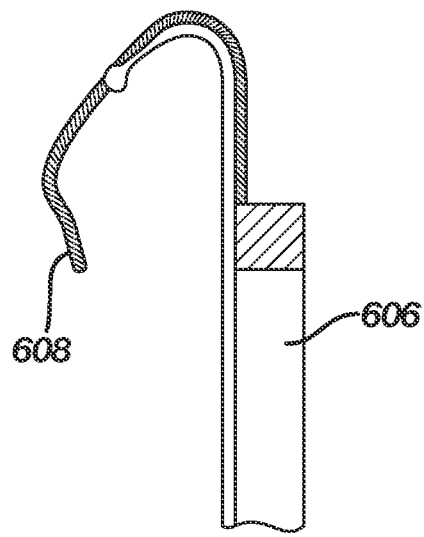
FIG. 13B depicts a side view of the exemplary guide catheter system of FIG. 13A with the guidewire in an extended position.
Figure 14A:
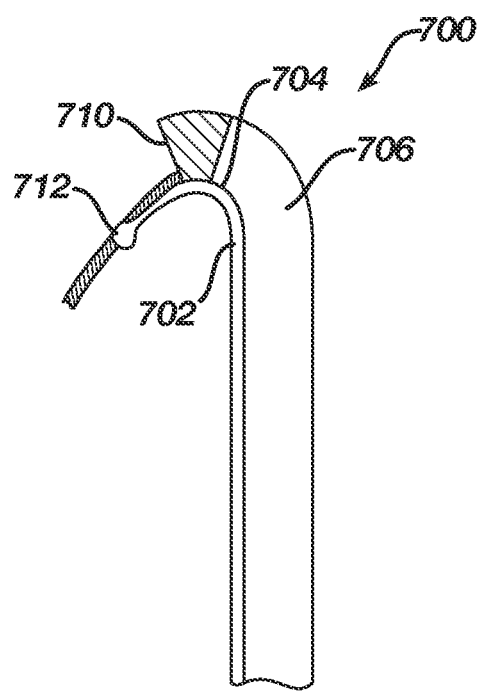
FIG. 14A depicts a side view of an exemplary guide catheter system according to the invention.
Figure 14B:
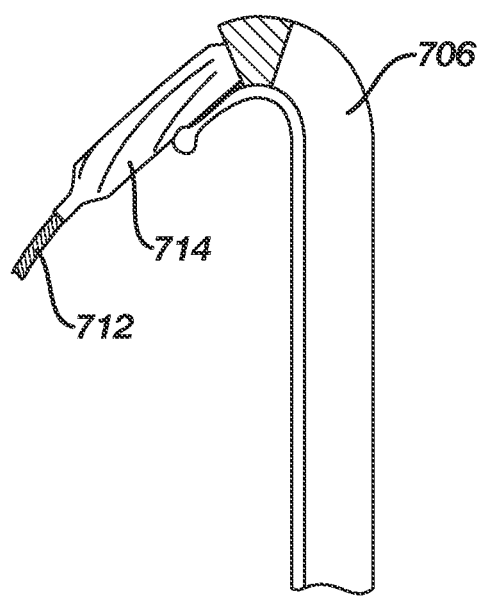
FIG. 14B depicts a side view of the exemplary guide catheter system of FIG. 14A with the dilation catheter in an extended position.

FIG. 12 shows a further exemplary sphenoid guide catheter (500) according to the invention. This guide catheter (500) provides for guide catheter placement into tight anatomical regions and for removal and reinsertion of an endoscope in an atraumatic fashion, that is, without damaging tissue of the sphenoid sinus or sphenoid sinus passageway.

As shown in FIG. 12, the guide catheter (500) has a balloon catheter tube (502) and an endoscope tube (504). The balloon catheter tube (502) has a proximal end (506) and a distal end (508) and an elongate shaft (510) between the proximal end (506) and the distal end (508). The endoscope tube (504) has a proximal end (512) and a distal end (514) and an elongate shaft (516) between the proximal end (512) and the distal end (514). The distal end of the guide catheter (500), which includes the distal ends of the balloon catheter tube (502) and the endoscope tube (504) is particularly designed for the sphenoid sinus to have a smaller profile than that of the combined proximal ends of the balloon catheter tube and the endoscope. The guide catheter (500) is constructed a soft polymeric material, i.e. from materials including but not limited to polyether block amide polymer and nylon. Following placement of the guide catheter (500) an endoscope is inserted into the proximal end (512) of the endoscope tube (504), opening up the endoscope tube lumen (520) and a balloon catheter is inserted into the proximal end (506) of the balloon catheter tube (502), opening up the balloon catheter tube lumen (518). A fitting that may be a screw fitting or a friction fitting may be included at the proximal end of the balloon catheter tube or the endoscope to for attachment of the devices to the guide catheter.

G. Alternative Exemplary Guide Catheter Systems

An alternative guide catheter system (600, 700) is shown, for example, in FIGS. 13A, 13B, 14A and 14B. In these embodiments, a probe (602, 702) that can be constructed of a rigid or semi-rigid material such as stainless steel 304 or nitinol is included on the inside of the curve (704) of the guide catheter (606, 706), which probe (602, 702) protrudes from between about 1 mm to 5 mm at its distal end (608, 708) from the distal end (610, 710) of the guide catheter (606, 706). The probe can be fixed to the guide catheter or can be translated within the guide catheter so that it can be longer or shorter. The probe allows the user to probe for the natural ostia and direct the guidewire (612, 712) to the user specified location. A groove on the probe tip may cover more than 180° of the guidewire to enable clipping of the guidewire into the probe. By positioning the guide catheter away from the curvature of the probe, the probe can be manipulated into place. A rib, ring, groove or added thickness soldered to the tip of the guidewire may be added to aid in retention of the guidewire in the probe until the probe is properly positioned. A retention feature on the probe contains the guidewire until the dilation catheter is inserted. Upon advancement of the dilation catheter over the guidewire, the guidewire is released from the retention feature on the rigid probe. Alternatively, a release mechanism on the proximal end of the guide catheter can be provided so that the user can affect release of the guidewire from the probe. Once the guidewire is in the appropriate position in the sinus as confirmed by transillumination the guide catheter is positioned into place over the probe. Once the guidewire is in position, the extension of the guide catheter around the curve of the probe creates a hood for the dilation catheter to push against to make a relatively sharp turn into the maxillary sinus (or other sinus). The dilation catheter is then inserted through the guide catheter and over the guide wire.

The probe can be manipulated with the hand or with a shaping tool for the appropriate sinus to be dilated or it can be pre-shaped. The probe can be permanently attached to a universal guide catheter (a 90° guide catheter) and angled to between 90 and 270° for use in the frontal, maxillary and/or sphenoid sinus.

H. Additional Alternative Exemplary Guide Catheter Systems

Figure 15:
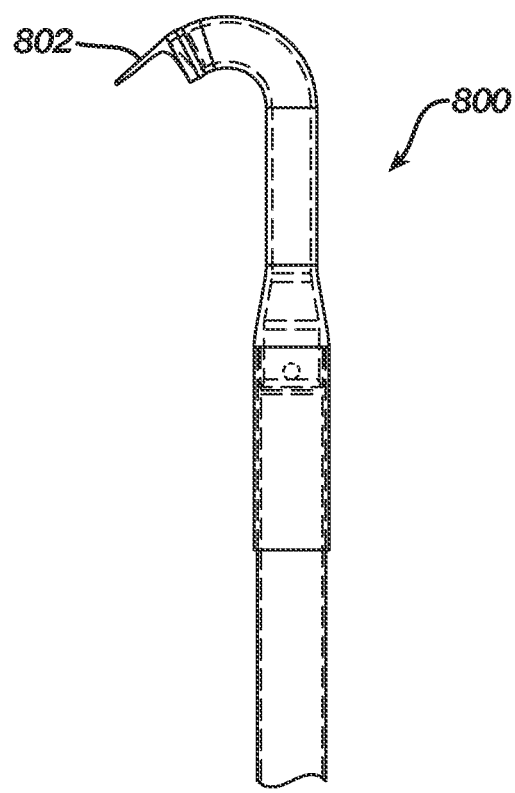
FIG. 15 depicts a side view of an exemplary guide catheter system according to the invention.

An additional alternative guide catheter system (800) is shown, for example, in FIG. 15. In this embodiment, the guide catheter tip (802) is improved by the addition of a thin-walled, flexible, polymeric hood. The material properties and dimensions are chosen such that the hood will deflect a relatively flexible guidewire but will itself be straightened out by a relatively stiff balloon catheter. For example, the hood can be made from 72D Pebax with a wall thickness of approximately 0.004 inches. It may be advantageous to include a small upward scoop at the very tip of the polymeric hood. The curvature of the swoop opens in the direction that is opposite that of the downward-deflecting primary hood curvature, and therefore reduces the potential for the balloon to catch on the distal tip when it is retracted. The tip curve also reduces the force needed to retract the balloon. It may be further advantageous to include a support member within the polymeric hood. The use of such a member allows for the selection of polymer material for the hood that is generally soft and flexible while still preserving the reliable and consistent guidewire deflection function. The support member may be metallic. It can be round in cross-section, i.e. a wire, or rectangular in cross-section, i.e. a ribbon. It can be formed from stainless steel or a super-elastic alloy such as nickel-titanium. It can have a consistent cross-sectional shape and size along its length or it can taper towards the distal end so as to have its greatest flexibility at its most distal point. The ribbon can be dimensioned and treated so as to provide a "bi-stable" functionality. In such an embodiment, the hood would remain in its downward-deflecting position until a threshold of upwardly directed force was surpassed, at which point the hood would "flip" to an upwardly deflected stable position. Following this sequence, the guide catheter system (800) could be removed from the nose and manually reset to its first stable position or this could be accomplished by manipulation of the guide against internal nasal structures.

IV. Overview of Exemplary Method for a Dilation Catheter System

The exemplary dilation catheter system (10) shown in FIG. 1 may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). As noted above, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (0) (or some other targeted anatomical passageway). After dilator (22) has been positioned within the ostium (0), dilator (22) may be inflated, thereby dilating the ostium.

In an alternative method, in order to deflect the guidewire tip to a steeper trajectory than provided by the guide catheter itself, the tip of the dilation catheter (20), which has been advanced along the guidewire (50), is advanced to a point inside the curve of the guide catheter (30). The dilation catheter tip is stiff enough to push the center of the guidewire curve closer to the guide, thereby resulting in a steeper trajectory. The trajectory angle can be increased by approximately 10-20 degrees. Since the guidewire angle trajectory can be activated by advancing and/or retracting the dilation catheter a given distance, a dilation catheter advancement mechanism may include a detent or mark to achieve the desired device wire angle trajectory and resulting dilation catheter position.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guide catheter system for use in treating a sinus cavity or a Eustachian tube, the system comprising: (a) a guide catheter comprising a proximal end, a distal end, and an elongate shaft between the proximal end and the distal end; and (b) a guidewire; wherein the guide catheter further comprises an opening having a groove formed therein at a distal tip of the distal end of the guide catheter for deflecting the guidewire at a predetermined angle, wherein the distal end has a first wall thickness, wherein the groove has a second wall thickness that is less than the first wall thickness of the distal end, wherein the groove is sized and configured to retain the guidewire and prevent lateral movement of the guidewire as the guidewire is moved relative to the groove through the opening.

2. The system of claim 1, wherein the sinus cavity is the maxillary sinus cavity and wherein the groove is sized and configured to deflect the guidewire at an angle of between 105° and 130°.

3. The system of claim 1, wherein the sinus cavity is the frontal sinus cavity and wherein the groove is sized and configured to deflect the guidewire at an angle of between 65° and 85°.

4. The system of claim 1, wherein the proximal end, the distal end, and the elongate shaft are formed from molded plastic and the guide catheter further comprises an atraumatic distal tip.

5. The system of claim 1, wherein the proximal end, the distal end, and the elongate shaft are formed from stainless steel and the guide catheter further comprises an atraumatic distal tip.

6. The system of claim 1, wherein the distal tip of the guide catheter is dimensioned to optimize positioning of the guidewire toward the maxillary sinus and deflection of the guidewire as the guidewire exits from the distal end of the guide catheter.

7. The system of claim 1, wherein the opening and the groove are both disposed at the distal tip of the guide catheter.

8. The system of claim 1, wherein the second wall thickness decreases moving distally toward the distal tip.

9. The system of claim 1, wherein the guidewire is retained in the groove and is prevented from lateral movement as the guidewire slides in the groove when advanced distally or retracted proximally through the opening thereby facilitating centering of the guidewire within the opening of the guide catheter.

10. The system of claim 9, wherein the groove includes opposing sidewalls are configured to contact the guidewire as the guidewire is advanced distally to prevent lateral movement of the guidewire in the groove.

11. The system of claim 1, wherein the opening comprises an oval-shaped opening, wherein the oval-shaped opening is disposed proximal to the groove.

12. The system of claim 11, wherein the oval-shaped opening has a width of between 2 mm and 3 mm and a length of between 3 mm and 6 mm.

13. The system of claim 11, wherein the oval-shaped opening has a width of between 2 mm and 3 mm and a length of between 5 mm and 9 mm.

14. The system of claim 11, wherein the groove retains the guidewire in the center of the oval-shaped opening.

15. A method for deflecting a guidewire to a predetermined angle, the method comprising: (a) providing a guide system comprising a guide catheter and guidewire, wherein the guide catheter includes an opening having a groove formed therein at a distal tip of the guide catheter for deflecting the guidewire to the predetermined angle, wherein the groove is formed into a wall of the distal tip of the guide catheter to thereby reduce the thickness of the wall; (b) inserting the guide system into a patient's nasal cavity; and (c) advancing the guidewire through the opening and the groove such that the guidewire is deflected at the predetermined angle into a desired sinus cavity, wherein the guidewire is retained in the groove and is prevented from lateral movement as the guidewire slides distally in the groove.

16. The method of claim 15, wherein the sinus cavity is the maxillary sinus cavity and wherein the groove deflects the guidewire at an angle of between 105° and 130°.

17. The method of claim 15, wherein the sinus cavity is the frontal sinus cavity and wherein the groove deflects the guidewire at an angle of between 65° and 85°.

18. The method of claim 15, wherein the distal tip of the guide catheter has a hooked shape, wherein inserting the guide system into a patient's nasal cavity further comprises sliding the hooked shape distal tip around uncinate process in the patients nasal cavity to direct the guidewire at the predetermined angle.

19. The method of claim 15, further comprising:
retracting the guidewire through the groove such that the guidewire is deflected at the predetermined angle from a desired sinus cavity, wherein the guidewire is retained in the groove and is prevented from lateral movement as the guidewire slides proximally in the groove.

20. The method of claim 12, wherein advancing the guidewire further comprises advancing the guidewire through the opening and the groove simultaneously.

21. The method of claim 15, wherein the wall is disposed the distal tip of the distal end, wherein the opening has a circumference, wherein the circumference has a first wall thickness, wherein the groove has a second thickness that is less than the first wall thickness.

22. The method of claim 15, wherein the opening comprises an oval-shaped opening, wherein the oval-shaped opening is disposed proximal to the groove.

23. The method of claim 22, wherein the oval-shaped opening has a width of between 2 mm and 3 mm and a length of between 3 mm and 6 mm.

24. The method of claim 22, wherein the oval-shaped opening has a width of between 2 mm and 3 mm and a length of between 5 mm and 9 mm.

25. A guide catheter system for use in treating a sinus cavity or a Eustachian tube, the system comprising:
(a) a guide catheter comprising a proximal end, a distal end, and an elongate shaft between the proximal end and the distal end, wherein a distal tip of the distal end includes an opening having a circumference, wherein the circumference has a first wall thickness; and
(b) a guidewire;
wherein the guide catheter further comprises a groove formed in the circumference of the guide catheter for deflecting the guidewire at a predetermined angle, wherein the groove has a second wall thickness that is less than the first wall thickness, wherein the groove is sized and configured to retain the guidewire and prevent lateral movement of the guidewire as the guidewire is moved relative to the groove through the opening.

26. The system of claim 25, wherein the distal tip of the guide catheter is dimensioned to optimize positioning of the guidewire toward the maxillary sinus and deflection of the guidewire as the guidewire exits from the distal end of the guide catheter.

27. The system of claim 25, wherein the opening is disposed proximal to the groove.

28. The system of claim 25, wherein the opening is an oval-shaped opening that flares outwardly moving distally such that an inside surface of the guide catheter meets an outside surface of the guide catheter system.

29. The system of claim 28, wherein the positioning of the guidewire in the groove and the geometry of the oval-shaped opening provide for the predetermined angle.

30. The system of claim 28, wherein the guidewire is centered in the oval-shaped opening.

\* \* \* \* \*